United States Patent
Lindner

(10) Patent No.: US 12,042,366 B2
(45) Date of Patent: Jul. 23, 2024

(54) ADHESIVE ATTACHMENT FOR ABSORBENT ARTICLE

(71) Applicant: The Procter & Gamble Company, Cincinnati, OH (US)

(72) Inventor: Torsten Lindner, Kronberg (DE)

(73) Assignee: The Procter & Gamble Company, Cincinnati, OH (US)

( * ) Notice: Subject to any disclaimer, the term of this patent is extended or adjusted under 35 U.S.C. 154(b) by 870 days.

(21) Appl. No.: 16/706,980

(22) Filed: Dec. 9, 2019

(65) Prior Publication Data

US 2020/0179188 A1   Jun. 11, 2020

Related U.S. Application Data

(60) Provisional application No. 62/777,425, filed on Dec. 10, 2018.

(51) Int. Cl.
*A61F 13/56* (2006.01)
*A61F 13/531* (2006.01)
*A61F 13/53* (2006.01)

(52) U.S. Cl.
CPC ........ *A61F 13/5611* (2013.01); *A61F 13/531* (2013.01); *A61F 13/5616* (2013.01); *A61F 2013/530802* (2013.01)

(58) Field of Classification Search
CPC .............. A61F 13/5611; A61F 13/5616; A61F 13/531; A61F 2013/530802
See application file for complete search history.

(56) References Cited

U.S. PATENT DOCUMENTS

| | | | |
|---|---|---|---|
| 4,336,804 A * | 6/1982 | Roeder | A61F 13/5611 604/387 |
| 4,460,364 A | 7/1984 | Chen | |
| 4,690,680 A * | 9/1987 | Higgins | A61F 13/5611 604/386 |
| 5,100,963 A | 3/1992 | Lin | |
| 5,459,193 A | 10/1995 | Anderson | |
| 5,591,153 A * | 1/1997 | Mattingly, III | A61F 13/5611 604/386 |
| 6,103,814 A | 8/2000 | Vandrongelen | |
| 6,280,557 B1 | 8/2001 | Peloquin | |
| D460,177 S * | 7/2002 | Endo | D24/125 |
| 6,465,557 B1 | 10/2002 | De | |
| D465,278 S * | 11/2002 | Endo | D24/125 |

(Continued)

FOREIGN PATENT DOCUMENTS

| | | | | |
|---|---|---|---|---|
| EP | 0528191 A1 | 2/1993 | | |
| EP | 0923921 A1 * | 6/1999 | | A61F 13/56 |

(Continued)

OTHER PUBLICATIONS

International Search Report and Written Opinion; Application Ser. No. PCT/US2019/065180; dated Mar. 16, 2020; 12 pages.

*Primary Examiner* — Susan S Su
(74) *Attorney, Agent, or Firm* — Amanda Herman Berghauer

(57) ABSTRACT

An absorbent article having improved adhesive attachment means to secure the absorbent article in the crotch region of a garment. The adhesive attachments means of this invention consists of an adhesive exhibiting reduced migration.

17 Claims, 2 Drawing Sheets

(56) References Cited

U.S. PATENT DOCUMENTS

| | | | |
|---|---|---|---|
| D465,570 S * | 11/2002 | Endo | D24/124 |
| 7,842,022 B2 | 11/2010 | Veglio | |
| 8,029,483 B2 | 10/2011 | Bonelli | |
| 9,439,817 B2 * | 9/2016 | Nishimura | A61F 13/5611 |
| 9,556,366 B2 † | 1/2017 | Bunnelle | |
| 9,980,856 B2 * | 5/2018 | Wilson | A61F 13/474 |
| 11,058,590 B2 * | 7/2021 | Toro | A61F 13/514 |
| 2003/0168165 A1 | 9/2003 | Hatfield | |
| 2005/0256481 A1 | 11/2005 | Rosati | |
| 2006/0229411 A1 | 10/2006 | Hatfield | |
| 2007/0043330 A1 | 2/2007 | Lankhof | |
| 2010/0035014 A1 * | 2/2010 | Hammons | A61F 13/4751 |
| | | | 428/156 |
| 2010/0217216 A1 | 8/2010 | Sue et al. | |
| 2013/0036802 A1 * | 2/2013 | Johnson | A61F 13/42 |
| | | | 73/74 |
| 2015/0038936 A1 | 2/2015 | Austin | |
| 2015/0328059 A1 * | 11/2015 | Robles | A61F 13/532 |
| | | | 604/378 |
| 2015/0351977 A1 * | 12/2015 | Bunnelle | C08L 23/12 |
| | | | 604/366 |
| 2017/0165133 A1 | 6/2017 | Turner | |

FOREIGN PATENT DOCUMENTS

| | | | |
|---|---|---|---|
| EP | 1181917 A2 | | 2/2002 |
| GB | 2473227 A | | 3/2011 |
| WO | 2009155265 A2 | | 12/2009 |
| WO | 2010138142 A1 † | | 12/2010 |
| WO | 2018145257 A1 † | | 8/2018 |

\* cited by examiner
† cited by third party

ADHESIVE ATTACHMENT FOR ABSORBENT ARTICLE

FIELD OF THE INVENTION

This invention relates generally to absorbent articles designed to be worn in the crotch region of a garment and, more particularly, to absorbent articles having non-migrating adhesives.

BACKGROUND OF THE INVENTION

Absorbent articles such as sanitary napkins, pantiliners, and incontinent pads are designed to absorb and retain liquid discharges from the human body and to prevent body and clothing soiling. In order to prevent soiling, such absorbent articles must be securely maintained in close proximity to and in conformity with the body of the wearer. The maintenance of the article against the body is known as "good body contact". Good body contact enables the absorbent article to absorb the vast majority of body fluids before they have an opportunity to flow quickly along the top surface of the article or the skin of the wearer, thereby preventing clothing and body soiling.

In order to securely maintain such absorbent articles in close proximity to the body of the wearer, it has become common for sanitary napkins and other absorbent articles that are designed to be worn in the crotch region of an undergarment or other garment to be secured in the crotch region by adhesive attachment means. The adhesive attachment means usually comprise a pressure sensitive adhesive disposed on the bottom surface of the article.

One issue with adhesives is their degradation over time due to temperature and due to exposure to oxygen. Additionally, adhesive can migrate through a film layer into an absorbent article. All of these reduce the effectiveness of the adhesive and its ability to adhere the absorbent article to the crotch of a panty. As such, there exists a need to create an absorbent article that utilizes an adhesive that does not migrate into the absorbent article through the film backsheet.

SUMMARY OF THE INVENTION

The present invention provides a sanitary absorbent article having improved adhesive attachment means to secure the absorbent article in the crotch region of a garment.

A sanitary absorbent article is disclosed. The sanitary absorbent article having an absorbent core with opposite longitudinal sides and opposite transverse ends and an adhesive attachment means on a garment faceable surface for securing the article to an undergarment. The adhesive attachment means comprises a weight average molecular weight of the low molecular weight component between 400 and 700 Daltons and between 0% and 20% of a low molecular weight component, based on the total weight of the adhesive attachment means.

A sanitary absorbent article is disclosed. The sanitary absorbent article having an absorbent core having high internal phase emulsion foam with opposite longitudinal sides and opposite transverse ends and an adhesive attachment means on a garment faceable surface for securing the article to an undergarment. The adhesive attachment means comprises a weight average molecular weight of the low molecular weight component between 400 and 700 Daltons and between 0% and 20% of a low molecular weight component, based on the total weight of the adhesive attachment means.

While the specification concludes with claims particularly pointing out and distinctly claiming the subject matter which is regarded as forming the present invention, it is believed that the invention will be better understood from the detailed description appearing in the following section taken in conjunction with the accompanying drawings.

DETAILED DESCRIPTION OF THE INVENTION

Figure 1:
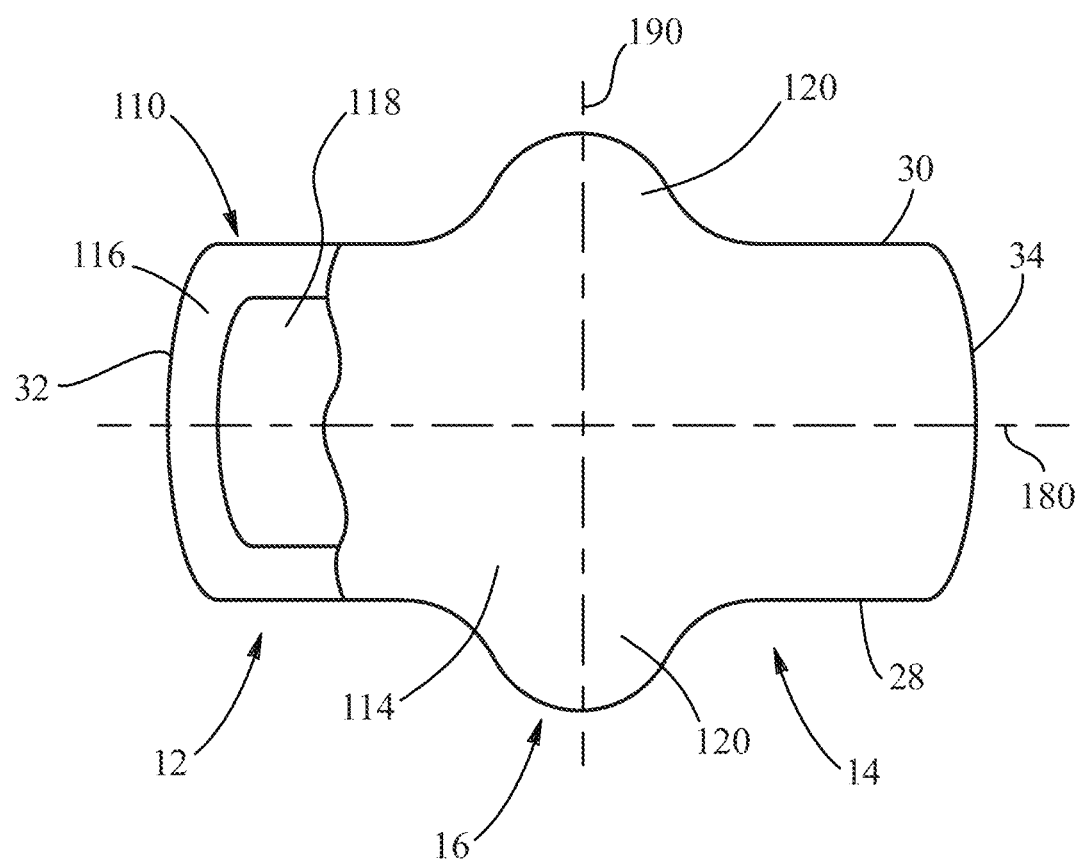
FIG. 1 is a view of an absorbent article in accordance with the present invention with a partially cut-away section to illustrate the construction of the article.

A preferred embodiment of the disposable absorbent article of the present invention, sanitary napkin 110, is shown in FIG. 1. As used herein the term "disposable absorbent article" refers to articles which absorb and contain body exudates and more specifically refers to articles which are placed against or in proximity to the body of the wearer to absorb and contain the various exudates discharged from the body, and to articles which are intended to be discarded after a single use (i.e., they are not intended to be laundered or otherwise restored or reused). As illustrated in FIG. 1, the sanitary napkin 110 is an elongated absorbent article intended to be maintained in a woman's crotch region to absorb vaginal discharges such as menses. It should be understood, however, that the present invention is also applicable for use in other disposable absorbent articles such as incontinent pads and the like.

As shown in FIG. 1, the sanitary napkin 110 has a longitudinal axis 180 and transverse axis 190. Sanitary napkin 110 first end region 12, a second end region 14 and a central region 16 disposed between each of the end regions. The sanitary napkin 110 comprises an absorbent core 118 having a garment-facing side and a body-facing side, a backsheet 116 disposed on the garment-facing side of the absorbent core 118, and adhesive attachment means disposed on the backsheet 116. In other preferred embodiments of the present invention, the sanitary napkin 110 can be optionally provided with additional elements as are known in the art, including a topsheet disposed on the body-facing side of the absorbent core 118, a removable release liner covering the adhesive attachment means in order to keep the adhesive from drying out or sticking to a surface other than the crotch portion of the garment prior to use, and wicking layers disposed between the absorbent core 118 and either the topsheet, the backsheet 116 or both.

While the sanitary napkin 110 can have any shape known in the art, a preferred embodiment of the sanitary napkin 110, which is illustrated in FIG. 1, has generally straight longitudinal edges 28 and 30 and rounded ends 32 and 34. However, any convenient design known to those skilled in the art can be used in the practice of the present invention. The sanitary napkin can, for example, have a generally hourglass shape wherein the longitudinal edges are curvilinear and the central region is narrower in the transverse direction than are the end regions. Such a design is generally illustrated in U.S. Pat. No. 4,324,246 issued to Mullane and Smith on Apr. 13, 1982. The present invention can also be used with the compound sanitary napkin described in U.S. Pat. No. 4,425,130 issued to Des Marais on Jan. 10, 1984. Further, the present invention can be used with the form of a sanitary napkin having side panels described in U.S. Pat. No. 4,285,343 issued to McNair on Aug. 25, 1981. Each of these three patents being herein incorporated by reference.

The central region 16 is that area of the sanitary napkin 110 which is generally located directly below the perineum of the wearer and which receives the greatest amount of menses. The first end region 12 and the second end region 14 extend outwardly from the central region toward the ends 32 and 34 respectively, of the sanitary napkin 110 a distance from about ⅛th to about ⅓rd of the total length of the sanitary napkin 10; although the exact size of the first and second end regions will vary according to the precise design and intended positioning of the sanitary napkin.

To provide means for absorbing body fluids, the sanitary napkin 110 is provided with an absorbent core 118. The absorbent core 118 has a garment-facing side and a body-facing side. The absorbent core 118 can be any means which is generally compressible, conformable, nonirrating to the wearer's skin, and capable of absorbing and retaining fluids and certain body exudates. The absorbent core 118 can be formed from any of the materials well known to those of ordinary skill in the art. Examples of such materials include multiple plies of creped cellulose wadding, fluffed cellulose fibers, wood pulp fibers or comminuted wood pulp fibers which is generally referred to airfelt, textile fibers, a blend of fibers, a mass or batt of fibers, a web of polymeric fibers, a blend of polyester and polypropylene fibers, absorbent foams, absorbent sponges, superabsorbent polymers, or any equivalent material or combination of materials. The total absorbent capacity of the absorbent core should, however, be compatible with the design exudate loading and the intended use of the sanitary napkin 10. Further, the size and absorbent capacity of the absorbent core 118 can be varied. Therefore, the dimensions, shape, and configuration of the absorbent core 118 can be varied (e.g. the absorbent core 118 can have a varying caliper, or a hydrophilic gradient, or can contain superabsorbent materials).

The absorbent core 118 is preferably a mass or batt of fibers. While many types of fibers can be used, a preferred material is a batt of polyester fibers.

The backsheet 116 is associated with the absorbent core 118 and is preferably attached thereto by attachment means (not shown) such as those well known in the art. For example, the absorbent core 118 can be secured to the backsheet 116 by a uniform continuous layer of adhesive, a patterned layer of adhesive, or an array of separate lines or spots of adhesive. An adhesive which has been found to be satisfactory is manufactured by Eastman Chemical Products Company of Kingsport, Tenn. and marketed under the tradename Eastobond A-3.

While the backsheet 116 can be formed in many different ways as are known in the art, a preferred backsheet 116 is impervious to liquid and is manufactured from a thin plastic film, although other flexible liquid impervious materials can also be used. The backsheet 116 prevents the liquids absorbed and contained in the absorbent core 118 from wetting articles which contact the sanitary napkin 110 such as undergarments. Suitable materials are well known in the art, including woven and nonwoven fabrics which have been treated to render them liquid repellent. Breathable or vapor pervious, liquid resistant materials, such as those materials described in U.S. Pat. No. 3,881,489 issued to Hartwell on May 6, 1975, and U.S. Pat. No. 3,989,867 issued to Sisson on Nov. 2, 1976 can also be used. These patents are incorporated herein by reference. Preferred materials are those materials that are fluid and vapor impervious, because they provide additional fluid strikethrough protection. Especially preferable materials include formed thermoplastic films. One especially suitable material is a polyethylene film having a thickness of from about 0.075 mils to about 1.25 mils, with a 1.0 mil thickness polyethylene film being especially suitable.

The backsheet 116 can alternatively be formed from a fluid previous layer overlying a liquid impervious layer. A preferred material for the liquid pervious material is a soft, smooth, compliant, liquid previous material as is known in the art. Those skilled in the art can readily select woven and nonwoven materials useful for this purpose, though nonwoven materials are preferred. For example, porous materials used as topsheets for disposable diapers or as coverings for conventional sanitary napkins can be used in the present invention. Useful liquid pervious layers are described in U.S. Pat. No. 4,341,217 issued to Ferguson and Landrigan on Jul. 27, 1982, and in U.S. Pat. No. 4,342,314 issued to Radel and Thompson on Aug. 3, 1982, both patents being incorporated herein by reference. The backsheet may be secured to the absorbent core by a uniform continuous layer of adhesive, a patterned layer of adhesive, or an array of separate lines, spirals, or spots of adhesive.

Disposed on the backsheet 116 is the adhesive attachment means. The adhesive attachment means are formed by coating the outer surface of the backsheet 116 with adhesive.

The adhesive attachment means can consist of an adhesive pattern having the shape of a block "I". The block "I" adhesive pattern is defined as having a base adhesive portion disposed in the first end region 12, a stem adhesive portion centrally disposed in the central region 16, and a head adhesive portion disposed in the second end region 14. It is essential that the adhesive attachment means consist of all three adhesive portions so that the benefits discussed herein may be realized.

The base adhesive portion is the generally rectangular zone that is disposed in the first end region 12 of the sanitary napkin 110. The base adhesive portion 36 provides a wide adhesive area extending transversely across the first end region 12 so as to prevent shifting or bunching of the sanitary napkin 110. The base adhesive portion preferably comprises a majority of the effective adhesive area available in the first end region 12.

That is, the area of the base adhesive portion should comprise at least about fifty percent (50%) of the effective adhesive area of the first end region 12. (The effective adhesive area being defined as that area of the other surface of the backsheet available to have adhesive applied thereto.) In addition, the base adhesive portion is preferably centrally located in the first end region 12 with respect to the longitudinal edges 28 and 30 of the sanitary napkin 110. That is, the base adhesive portion should be equidistantly inwardly spaced from the longitudinal edges of the sanitary napkin 110 in the first end region 12 so that adhesive does not contact the skin of the wearer. The base adhesive portion should also preferably terminate before the end of the first end region 12 so that adhesive will not touch the wearer. Preferably, the base adhesive portion is inwardly spaced at least about 0.25 inches (about 6 mm) from the longitudinal edges 28 and 30 and at least about 0.5 inches (about 12 mm) from the end 32 in the first end region 12.

The exact adhesive pattern of the base adhesive portion can widely vary and take on a number of adhesive configurations such as an array of discrete adhesive elements. For example, the base adhesive portion can comprise a multiplicity of discrete adhesive elements such as adhesive strips, circles, triangles, or any other shaped adhesive pieces arranged in either a random or regular pattern which provides a wide zone of adhesive. While the size, arrangement and disposition of adhesive within the base adhesive portion may vary, the base adhesive portion preferably comprises a relatively wide strip of adhesive that extends transversely across the first end region 12.

The stem adhesive portion is the relatively narrow rectangular adhesive zone that is centrally disposed in the central region 16 of the sanitary napkin 110. The stem adhesive portion provides a narrow adhesive area extending longitudinally in the central region 16 of the sanitary napkin 110 to allow for initial pad bunching and secure attachment of the sanitary napkin 110 in the central region 16.

The exact adhesive pattern of the stem adhesive portion can widely vary and take on a number of adhesive configurations such as an array of discrete adhesive elements. For example, the stem adhesive portion can comprise a multiplicity of discrete adhesive elements such as adhesive strips, circles, triangles, or any other shaped adhesive pieces arranged in either a random or regular pattern which provide a narrow zone of adhesive. It should be noted that the adhesive elements that comprise the stem adhesive portion can also serve as portions of either the base or head adhesive within the stem adhesive portion. The stem adhesive portion preferably comprises a relatively narrow strip of adhesive centrally disposed with respect to the longitudinal edges of the sanitary napkin and extending longitudinally along the sanitary napkin.

The head adhesive portion is the generally rectangular zone that is disposed in the second end region 14 of the sanitary napkin 110. The head adhesive portion provides a wide adhesive area extending transversely across the second end region 14 so as to prevent shifting or bunching of the sanitary napkin 110. The head adhesive portion preferably comprises a majority of the effective adhesive area available in the second end region 14. That is, the area of the head adhesive portion should comprise at least about fifty percent (50%) of the effective adhesive area of the second end region 14. In addition, the head adhesive zone is preferably centrally located in the second end region 14 with respect to the longitudinal edges 28 and 30 of the sanitary napkin 110. That is, the head adhesive portion should be equidistantly inwardly spaced from the longitudinal edges 28 and 30 of the sanitary napkin in the second end region 14 so that adhesive does not contact the skin of the wearer. The head adhesive portion should also preferably terminate before the end edge 34 of the second end region 14 so that adhesive will not touch the wearer. Preferably, the head adhesive portion is inwardly spaced at least about 0.25 inches (about 6 mm) from the longitudinal edges 28 and 30 of the sanitary napkin 110 in the second end region 14 and at least about 0.5 inches (about 12 mm) from the second end.

In use, the sanitary napkin 110 or sanitary absorbent article is secured on the inside of the crotch portion of a garment with the adhesive side toward the crotch. It is secured in position by pressing the adhesive attachment means firmly against the crotch material. The adhesive is entirely within the margin of the sanitary napkin, so that there is no possible contact with the body of the wearer.

The absorbent core may be any absorbent means capable of absorbing or retaining liquids (e.g., menses and/or urine). The absorbent core may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester or polyolefin fibers; peat moss; tissue including tissue wraps and tissue laminates; absorbent foams; absorbent sponges; superabsorbent polymers; absorbent gelling materials; or any equivalent material or combinations of materials, or mixtures of these. The absorbent core may have more than one layer wherein each layer may be identical or distinct in one or more property or composition from another layer. A particularly preferred absorbent core is made of thermally bonded airlaid material having less than 50 percent synthetic fibers. Synthetic fibers are preferred due to the ease with which they fuse together to join the core and topsheet as described below. A particularly preferred synthetic fiber is a bi-component material having a polyethylene sheath and a polypropylene center.

The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, panty liners, regular sanitary napkins, or overnight sanitary napkins.

The fluid absorbent material can be constructed from any of a variety of materials commonly used in disposable absorbent articles. Examples of suitable absorbent materials include creped cellulose wadding, cotton fluff, and citric acid cross-linked cellulose pulp disclosed in U.S. Pat. No. 5,190,563, issued Mar. 2, 1993, U.S. Pat. No. 5,183,707, issued Feb. 2, 1993; and U.S. Pat. No. 5,137,537, issued Aug. 11, 1992, all issued to Herron et al.; synthetic fibers disclosed in U.S. Pat. No. 4,578,414, Sawyer, issued Mar. 25, 1986; absorbent foams, absorbent sponges, superabsorbent composites, superabsorbent foam, and super absorbent polymers. A preferred fluid absorbent material is comminuted and airlaid wood pulp fibers commonly referred to as absorbent fluff. An absorbent fluff having a density of from about 0.05 g to about 0.175 g per $cm^3$ is generally acceptable.

The absorbent core structure may comprise a substrate and superabsorbent polymer layer as those described in U.S. Pat. No. 8,124,827 filed on Dec. 2, 2008 (Tamburro); U.S. application Ser. No. 12/718,244 published on Sep. 9, 2010; U.S. application Ser. No. 12/754,935 published on Oct. 14, 2010; or U.S. Pat. No. 8,674,169 issued on Mar. 18, 2014.

The absorbent core may be an open-cell foam produced from the polymerization of monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photo-initiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking co-monomer, or cross-linker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of cross-linkers contain a mixture of acrylate and methacrylate moieties, such as ethylene glycol acrylate-methacrylate and neopentyl glycol acrylate-methacrylate. The ratio of methacrylate:acrylate group in the mixed cross-linker may be varied from 50:50 to any other ratio as needed.

Any third substantially water-insoluble co-monomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam.

These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type can have styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they can have between about 1% and about 20%, in certain embodiments from about 2% to about 15%, and in certain other embodiments from about 3% to about 12% by weight of the oil phase. In certain embodiments, co-emulsifiers may also be used to provide additional control of cell size, cell size distribution, and emulsion stability, particularly at higher temperatures, for example greater than about 65° C. Examples of co-emulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts. In certain embodiments, ditallow dimethyl ammonium methyl sulfate (DTDMAMS) may be used as a co-emulsifier.

The oil phase may comprise a photo-initiator at between about 0.05% and about 10%, and in certain embodiments between about 0.2% and about 10% by weight of the oil phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of about 200 nanometers (nm) to about 800 nm, in certain embodiments about 200 nm to about 350 nm. If the photo-initiator is in the oil phase, suitable types of oil-soluble photo-initiators include benzyl ketals, α-hydroxyalkyl phenones, α-amino alkyl phenones, and acylphospine oxides. Examples of photo-initiators include 2,4,6-[trimethylbenzoyldiphosphine] oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methyl thio) phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl) phenyl]propanone] (sold by Lamberti spa, Gallarate, Italy as ESACURE® KIP EM.

The dispersed aqueous phase of a HIPE can have water, and may also have one or more components, such as initiator, photo-initiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, co-monomers, and cross-linkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counter-ions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine) dihydrochloride, and other suitable azo initiators. In certain embodiments, to reduce the potential for premature polymerization which may clog the emulsification system, addition of the initiator to the monomer phase may be just after or near the end of emulsification.

Photo-initiators present in the aqueous phase may be at least partially water soluble and can have between about 0.05% and about 10%, and in certain embodiments between about 0.2% and about 10% by weight of the aqueous phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photo-initiator is in the aqueous phase, suitable types of water-soluble photo-initiators include benzophenones, benzils, and thioxanthones. Examples of photo-initiators include 2,2'-Azobis [2-(2-imidazolin-2-yl)propane]dihydrochloride; 2,2'-Azobis[2-(2-imidazolin-2-yl)propane]disulfate dehydrate; 2,2'-Azobis(1-imino-1-pyrrolidino-2-ethylpropane) dihydrochloride; 2,2'-Azobis[2-methyl-N-(2-hydroxyethyl)propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone,4-dimethylamino-4'-carboxymethoxydibenzalacetone; and 4,4'-disulphoxymethoxydibenzalacetone. Other suitable photo-initiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

Adhesive Type:

The backsheet may be secured to the absorbent core by a uniform continuous layer of adhesive, a patterned layer of adhesive, or an array of separate lines, spirals, or spots of adhesive.

The adhesive can be a panti fastener adhesive (PFA) with improved aging performance. The PFA adhesive can be used at levels such as, for example, between 10 and 50 gsm, such as, for example, 15 gsm, 20 gsm, 25 gsm, 30 gsm, 35 gsm, 40 gsm, 45 gsm, or 50 gsm.

Without being bound by theory, it has been found that PFA adhesives will migrate through the backsheet into the absorbent core. It is believed that the level of migration varies with the type and form of absorbent core. The migration of adhesive can reduce the effectiveness of the adhesive to a level that becomes measurable and affects the consumer interaction with the product.

When in combination with a HIPE core, Applicants have found that traditional PFAs can migrate into the core thereby reducing the effectiveness of the adhesive. Without being bound by theory, it is believed that the HIPE core acts as a thermodynamic sink for migration of the low molecular weight components for the adhesive. They end up on the—very large—internal surface of the FAM. The backsheet film (PE) is permeable to migration. To offset this effect, the PFA adhesive is traditionally increased by a factor of 2 to 2.5. Areas where there is the highest overlap with the HIPE core may have 35 gsm while areas with no direct overlap with the HIPE core may have up to 25 gsm.

As stated above, without being bound by theory, it is believed that there is a correlation with the pore size of the absorbent structures and the level of PFA migration. Specifically, it is believed that by selecting PFAs that increase the molecular weight of lower molecular components of the PFA formulation lead to reduced migration. This is because the use of higher molecular weight components of the PFA formulation can decrease the thermodynamic driving force for partitioning (less entropy gain): In the thermodynamic equilibrium, allowing more migrants to stay in the adhesive. As a side effect, lower molecular weight also decreases the diffusion coefficient of migrants in polymer matrices, i.e. slows down the migration process.

Said otherwise, without being bound by theory, it is believed that one can reduce the level of adhesive migration by selecting an adhesive that has less than 20% of low molecular weight components, such as, for example, between 0.5% and 20% of low molecular weight components, between 1% and 19% of low molecular weight components, such as, for example, 2%, 3%, 4%, 5%, 6%, 7%, 8%, 9%, 10%, 11%, 12%, 13%, 14%, 15%, 16%, 17%, 18% or 19% of low molecular weight components. As exemplified herein, low molecular weight components are components having a weight average molecular weight of up to 700 Daltons (Da), such as, for example, between 1 Da and 700 Da, between 400 Da and 700 Da, such as, for example 100 Da, 150 Da, 200 Da, 250 Da, 300 Da, 350 Da, 400 Da, 450 Da, 500 Da, 550 Da, 600 Da, or 650 Da. This is exemplified when comparing Henkel's Dispomelt 689B adhesive to Henkel's Dispomelt 6530 adhesive.

Table 1 summarizes Henkel's DISPOMELT 689B and 6530's weight average molecular weight of the low molecular weight component, its content in the adhesive, and its neat viscosity. It is believed that an adhesive containing less than 14 wt % of the low molecular weight component and a viscosity less than 500 mPa at 40° C. provide improved adhesive migration resistance to P&G's substrate. Both DISPOMELT 689B and 6530 are based on synthetic rubber-based resins with substantially similar components, with key difference as the low molecular weight content and viscosity.

TABLE 1

| | Henkel DISPOMELT 689B | Henkel DISPOMELT 6530 |
|---|---|---|
| Weight average molecular weight of the low molecular weight component | Mw: 400-700 Da | Mw: 400-700 Da |
| % of the low molecular weight component, based on the total weight of the adhesive | 20-26% | 1-14% |
| Kinematic viscosity of the low molecular weight component, measured at 40° C. in accordance with ASTM D0445 | 68 CST | 68 CST |

Figure 2:
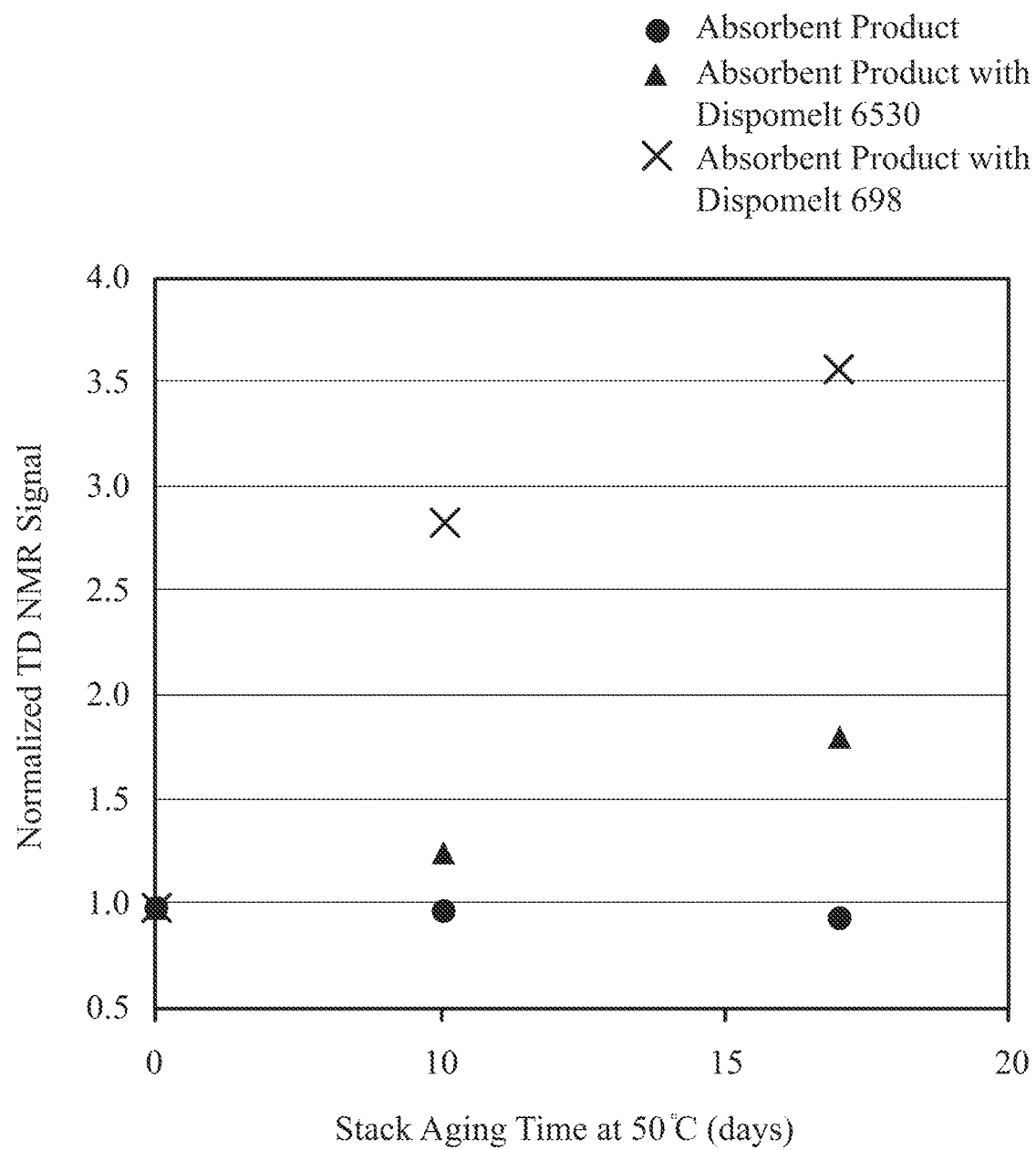
FIG. 2 is a graph showing the migration of adhesives into HIPE cores.

FIG. 2 shows a normal TD NMR signal for four HIPE Cores; one being a control and the others having different adhesives. The samples are aged at 50 degrees Celsius for different amounts of days. As shown in the graph, one can reduce the amount migration by changing the composition of the PFA adhesive. Compositions exhibiting a TD NMR signal greater than 2.0 exhibit high levels of migration. As shown in the graph, after only 5 days at 50 degrees Celsius, the product using Dispomelt 698 exhibits a high level of migration. The level of migration increase to greater than 3.5 at 10 days at 50 degrees Celsius for the Dispomelt 698. Unlike Dispomelt 698, Dispomelt 6530 does not exhibit a TD NMR greater than 2.0 at either 5 days or 10 days of storage at 50 degrees Celsius.

Without being bound by theory, it is believed that this demonstrate that the HIPE core acts as a thermodynamic sink for migration of the low molecular weight components for the adhesive. It is believed that they end up on the—very large—internal surface of the HIPE foam. The backsheet film (PE) is permeable to migration. Additionally it is believed that migration of low molecular weight components of the panty fastening adhesive (PFA) into the absorbent article core through the backsheet happens as well with non-HIPE foam containing products, but to a lesser extent as the thermodynamic sinks available in those products have a lower reservoir capacity compared to the internal surface of the HIPE foam. (Please note: capillary forces of the HIPE foam are not a driving force. The capillary forces would be by a factor of 1000 too low to pull dissolved species out of the adhesive.)

The effects of adhesive migration may also be shown using a PFA tack performance via a 180° peel test (target range: 2-7 N). In a 180° peel test, a cotton woven is applied to the backsheet under weight (planar rectangular shape) and then pulled away at r.t. In a variant of the method, the sample with the weight is left for 3 h at 37° C. before the peel test. The method is under discussion as it may not be fully indicative of the consumer experience.

Test procedure: 180° peel test (target range: 2-7 N).

PFA tack performance is currently measured via a 180° peel test (target range: 2-7 N). A cotton woven is applied to the backsheet under weight (planar rectangular shape) and then pulled away at controlled rate. In a variant of the method, the sample with the weight is left for 3 h at 37° C. before the peel test.

Equilibration is reached after 15 days at 49° C. (tests with stacked lab samples "PFA-Poly-FAM", separated via mylar sheets, no EVA adhesives). Equilibration at room temperature is assumed to happen within a time frame of 3 months.

Rationale for selecting a temperature of 49° C. for accelerated aging tests: Tests at 40° C. took too long to see an effect for the purpose of quick diagnosis. 60° C. was expected to thermally impact the backsheet polymer; this can additionally impact the peel force and may lead to convoluted data.

Combinations:
A. A sanitary absorbent article comprising an absorbent core with opposite longitudinal sides and opposite transverse ends, the absorbent article further including an adhesive attachment means on a garment faceable surface for securing the article to the undergarment, wherein the adhesive attachment means comprises a Weight average molecular weight of the low molecular weight component between 400 and 700 Daltons and between 0% and 20% of a low molecular weight component, based on the total weight of the adhesive attachment means.
B. The sanitary absorbent article of paragraph A, wherein the adhesive attachment means comprises a pattern including two longitudinally extending strips, one strip being located adjacent to each respective longitudinal side of the article and two laterally extending strips, one strip being located adjacent to each respective transverse end of the article said longitudinal extending strips and said laterally extending strips substantially surrounding a center region that is non-tacky at room temperature and is incapable of adhesively securing that portion of the garment faceable surface of the article to the wearer's undergarment in use.

C. The sanitary absorbent article of paragraph B, the two longitudinally extending strips contact the two laterally extending strips to fully enclose the center region.
D. The sanitary absorbent article of any of paragraphs B-C, wherein said center region has a length of from about 10 cm to about 12 cm.
E. The sanitary absorbent article of any of paragraphs A-D, wherein said sanitary absorbent article is a sanitary napkin.
F. The sanitary absorbent article of any of paragraphs B-E, wherein the two longitudinally extending strips are separated from and do not contact the two laterally extending strips.
G. The sanitary absorbent article of paragraph F, wherein the two longitudinally extending strips are intermediate the two laterally extending strips.
H. The sanitary absorbent article of paragraph G, wherein the two laterally extending strips are intermediate the two longitudinally extending strips.
I. The sanitary absorbent article of any of paragraphs B-H, wherein each longitudinally extending strips is inward from each respective longitudinal side.
J. The sanitary absorbent article of any of paragraphs A-I, wherein the adhesive means is placed on the garment facing side of the backsheet at a level between 10 and 30 gsm.
K. The sanitary absorbent article of any of paragraphs A-J, wherein the central absorbent agent comprises a High Internal Phase Emulsion foam.
L. The sanitary absorbent article of any of paragraphs A-K, wherein the absorbent article comprises a pair of flexible side flaps 120, one flap extending laterally outward from each respective longitudinal side of the absorbent element, the flaps being adapted to be folded over a crotch portion of a wearer's undergarment when in use.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A sanitary absorbent article comprising a topsheet, a backsheet, and an absorbent core with opposite longitudinal sides and opposite transverse ends, wherein the absorbent core is disposed between the topsheet and the backsheet, the absorbent article further including an adhesive attachment means on a garment faceable surface of the backsheet for securing the article to the undergarment, wherein the absorbent core comprises a High Internal Phase Emulsion foam, wherein the adhesive attachment means comprises between 1% and 14% of a low molecular weight component, based on the total weight of the adhesive attachment means, wherein the low molecular weight component has a Weight average molecular weight of between 400 and 700 Daltons and a kinematic viscosity measured at 40° C. of 68 CST, wherein the High Internal Phase Emulsion foam is an open-cell foam, wherein the adhesive attachment means is a rubber based resin.

2. The sanitary absorbent article of claim 1, wherein said sanitary absorbent article is a sanitary napkin.

3. The sanitary absorbent article of claim 1, wherein the adhesive means is placed on the garment faceable surface of the backsheet at a level between 10 and 30 gsm.

4. The sanitary absorbent article of claim 1, wherein the absorbent article comprises a pair of flexible side flaps, one flap extending laterally outward from each respective longitudinal side of the absorbent article, the flaps being adapted to be folded over a crotch portion of a wearer's undergarment when in use.

5. The sanitary absorbent article of claim 1, wherein the backsheet comprises a polyethylene film.

6. The sanitary absorbent article of claim 5, wherein the backsheet has a thickness of from about 0.075 mils to about 1.25 mils.

7. The sanitary absorbent article of claim 1, further comprising an adhesive disposed between the backsheet and the absorbent core.

8. The sanitary absorbent article of claim 7, wherein the adhesive is deposited in a uniform continuous layer of adhesive, a patterned layer of adhesive, or an array of separate lines, spirals, or spots of adhesive.

9. A sanitary absorbent article comprising an absorbent core with opposite longitudinal sides and opposite transverse ends, wherein the absorbent core comprises a high internal phase emulsion foam, the absorbent article further including an adhesive attachment means on a garment faceable surface for securing the article to the undergarment, wherein the adhesive attachment means comprises between 1% and 5% of a low molecular weight component, based on the total weight of the adhesive attachment means, wherein the low molecular weight component has a weight average molecular weight of between 400 and 700 Daltons, wherein the adhesive attachment means is a rubber based resin; wherein the adhesive attachment means exhibits a tack performance of 2-7 N in a 180° peel test.

10. The sanitary absorbent article of claim 9, wherein said sanitary absorbent article is a sanitary napkin.

11. The sanitary absorbent article of claim 9, wherein the absorbent article further comprises a top sheet and a backsheet, wherein the absorbent core is disposed between the topsheet and the backsheet, wherein the adhesive means is placed on the garment faceable surface of the backsheet at a level between 10 and 30 gsm.

12. The sanitary absorbent article of claim 9, wherein the absorbent core comprises a central absorbent agent, wherein the central absorbent agent comprises the High Internal Phase Emulsion foam.

13. The sanitary absorbent article of claim 9, wherein the High Internal Phase Emulsion foam is an open-cell foam.

14. The sanitary absorbent article of claim 9, wherein the backsheet comprises a polyethylene film.

15. The sanitary absorbent article of claim 14, wherein the backsheet has a thickness of from about 0.075 mils to about 1.25 mils.

16. The sanitary absorbent article of claim 9, further comprising an adhesive disposed between the backsheet and the absorbent core.

17. The sanitary absorbent article of claim 16, wherein the adhesive is deposited in a uniform continuous layer of adhesive, a patterned layer of adhesive, or an array of separate lines, spirals, or spots of adhesive.

* * * * *